United States Patent
Yagi et al.

(10) Patent No.: US 7,191,656 B2
(45) Date of Patent: Mar. 20, 2007

(54) SUBSTRATE CRACK INSPECTING METHOD, SUBSTRATE CRACK INSPECTION APPARATUS, AND SOLAR BATTERY MODULE MANUFACTURING METHOD

(75) Inventors: Katsuyuki Yagi, Nara (JP); Hiroshi Kanishi, Osaka (JP); Yoshikazu Kawagoe, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 184 days.

(21) Appl. No.: 10/965,743

(22) Filed: Oct. 18, 2004

(65) Prior Publication Data

US 2005/0097961 A1    May 12, 2005

(30) Foreign Application Priority Data

Nov. 10, 2003   (JP)   ............... 2003-379995

(51) Int. Cl.
*G01N 29/12* (2006.01)
*G01H 13/00* (2006.01)

(52) U.S. Cl. ............ 73/579; 73/12.01; 73/865.6; 73/571

(58) Field of Classification Search ............ 73/279, 73/12.01, 865.6, 571
See application file for complete search history.

(56) References Cited

U.S. PATENT DOCUMENTS

| | | | |
|---|---|---|---|
| 3,308,650 A * | 3/1967 | Fitzgerald | 73/571 |
| 4,879,905 A * | 11/1989 | Chen et al. | 73/579 |
| 4,884,696 A * | 12/1989 | Peleg | 209/545 |
| 5,195,046 A | 3/1993 | Gerardi et al. | |
| 5,214,960 A * | 6/1993 | Tsuboi | 73/579 |
| 5,285,687 A | 2/1994 | Ringel et al. | |
| 5,520,052 A * | 5/1996 | Pechersky | 73/579 |
| 6,450,036 B1 * | 9/2002 | Ashida et al. | 73/584 |

FOREIGN PATENT DOCUMENTS

| | | | |
|---|---|---|---|
| DE | 3842061 A1 * | 6/1990 | |
| JP | 2002166234 A * | 6/2002 | |
| JP | 2002-343989 | 11/2002 | |
| JP | 2002-343992 | 11/2002 | |
| WO | 01/33182 A1 | 5/2001 | |
| WO | 01/39253 A2 | 5/2001 | |

OTHER PUBLICATIONS

Thierry Debelle, "Making Sound Measurements and Octave Analysis", Aug. 18-20, 1999, National Instruments NIWeek, pp. 1-20, downloaded from www.natinst.com Jun. 14, 2004.*
European Search Report Mailed May 11, 2005 in corresponding EP application No. 040224566.4-2004.
Patent Abstracts of Japan, vol. 2002, No. 10, Oct. 10, 2002 & JP 2002 166234 A (Sharp Corp), Jun. 11, 2002.

* cited by examiner

*Primary Examiner*—Hezron Williams
*Assistant Examiner*—Rose M. Miller
(74) *Attorney, Agent, or Firm*—Nixon & Vanderhye P.C.

(57) ABSTRACT

Certain example embodiments of the present invention provide a method for detecting a substrate crack by simple equipment and steps. A substrate crack inspecting method may include the steps of (1) producing a sound by providing vibration to a substrate, (2) determining a power spectrum by capturing the produced sound and carrying out an acoustic analysis for the captured sound, and (3) judging whether or not a substrate crack exists based on a spectral intensity of a predetermined frequency region.

10 Claims, 9 Drawing Sheets

SUBSTRATE CRACK INSPECTING METHOD, SUBSTRATE CRACK INSPECTION APPARATUS, AND SOLAR BATTERY MODULE MANUFACTURING METHOD

CROSS-REFERENCE TO RELATED APPLICATION

This application is related to Japanese application No. 2003-379995 filed on Nov. 10, 2003 whose priority is claimed under 35 USC §119, the disclosure of which is incorporated by reference in its entirety.

BACKGROUND OF THE INVENTION

1. Field of the Invention

The present invention relates to a substrate crack inspecting (examining, testing) method, a substrate crack inspection apparatus, and a solar battery module manufacturing method, and in detail, it relates to a method for inspecting a substrate for a crack by analyzing a sound produced by providing vibration for a substrate, an apparatus suitable for the method, and a solar battery module manufacturing method by use of solar cells selected by the method.

2. Description of Related Art

A solar battery is generally manufactured by the following method. First, a solar battery cell is manufactured by forming a pn junction and a pair of electrodes on a silicon wafer obtained by slicing a silicon ingot. Next, by electrically connecting a plurality of solar battery cells by use of an interconnector, arrayed solar battery cells (array cells) are obtained. Next, tempered glass, a sealing resin, array cells, a sealing resin, and a back film are laminated in this order. Then, after connecting the adjacent arrayed cells to each other and attaching a power outlet terminal line, sealing processing is carried out. After the sealing processing is completed, by attaching a terminal box to the power drawout terminal line and attaching a frame, a solar battery module is completed. The completed solar battery module is factory-shipped after an inspection of output characteristics is carried out by use of a solar simulator.

Inside the silicon wafer which is a cell material for a solar battery cell, a minute crack called a microcrack, namely, internal alligatoring may occur during its production. The solar battery cells with internal alligatoring sometimes fracture in the steps for manufacturing a solar battery module. If a solar battery cell fractures, it is necessary to carry out a restoring step to remove the fractured cell and mount another solar battery cell. As a result of an addition of a new operation as such, productivity of the solar battery modules declines. In addition, even when the aforementioned solar battery cells with microcracks are mounted without fracturing and completed as a solar battery module, the solar battery cells with microcracks are insufficient in power generating performance, therefore, in the completed solar battery module, a problem such as a decline in the power output as a whole occurs.

As a conventional method for detecting a microcrack, known is a method of previously applying to a substrate a stress substantially the same as a stress that the substrate receives at the time of a predetermined processing, adding another shock to the substrate, and detecting whether or not damage exists based on a produced sound (see Japanese Unexamined Patent Publication No. 2002-343989, for example.)

However, according to the conventional method, since an apparatus for applying a stress to the substrate is necessary, the manufacturing equipment is complicated, and a problem exists such that production efficiency declines.

SUMMARY OF THE INVENTION

The present invention has been made in view of such circumstances and provides a method for detecting a substrate crack by simple equipment and steps.

A substrate crack inspecting method according to the present invention comprises the steps of (1) producing a sound by providing vibration for a substrate, (2) determining a power spectrum by capturing the produced sound and carrying out an acoustic analysis for the captured sound, and (3) judging whether or not a substrate crack exists based on a spectral intensity of a predetermined frequency region.

The inventor has discovered that a spectral intensity becomes great at a predetermined frequency region indicating presence of substrate crack(s) when, in terms of a substrate with a crack, a power spectrum is determined by the method as described above, and thereby completed the present invention.

According to the present invention, a substrate crack can be detected by simple equipment and steps.

In addition, the method of the present invention can be used for a silicon wafer obtained by slicing a silicon ingot, and in this case, a substrate with a substrate crack can be eliminated from the manufacturing steps before manufacturing a solar battery cell, whereby the production efficiency can be improved.

In addition, the method of the present invention can be used for a solar battery cell, and in this case, a solar battery cell with a substrate crack can be eliminated from the module manufacturing steps. Thereby, a fracture that occurs in the solar battery module manufacturing steps can be prevented beforehand, and this can greatly contribute in preventing a decline in the yielding percentage and a decline in the rate of operation in the same steps. In addition, the wastefulness of a restoring step to remove a fractured cell and mount another solar battery cell can be eliminated.

DESCRIPTION OF THE PREFERRED EMBODIMENTS

A substrate crack inspecting method according to a first embodiment of the present invention comprises the steps of (1) producing a sound by providing vibration for a substrate, (2) determining a power spectrum by capturing the produced sound and carrying out an acoustic analysis for the captured sound, and (3) judging whether or not a substrate crack exists based on a spectral intensity of a predetermined frequency region.

First, description will be given of the step (1), namely, a step of producing a sound by providing vibration for a substrate.

For the substrate, an elemental semiconductor substrate of Si, Ge, etc., a compound semiconductor substrate of GaAs, GaN, GaP, InP, ZnO, ZnSe, etc., and a glass substrate can be used. Concretely, for example, a silicon polycrystalline or monocrystalline substrate with a size of an approximately 126 mm-square and a thickness of approximately $200\mu\sim300\mu$ can be used.

In addition, as the substrate, a substrate in which impurities have been doped to form a pn junction, furthermore, a substrate with electrodes formed, and moreover, a substrate with desirable thin film(s) formed and a substrate to which desirable processing(s) have been applied are also included. In a case of a silicon solar battery, a silicon wafer obtained by slicing a silicon ingot and a solar battery cell obtained by forming a pn junction and electrodes on a silicon wafer are also included.

As a method for providing vibration for the substrate, a method for providing vibration for a substrate by, while supporting a predetermined position of the substrate, striking the substrate with an elastic member is preferably used. For the "elastic member," synthetic rubber, urethane rubber, silicone rubber, etc., can be used. In addition, the elastic member preferably has a front end of a curved surface shape. According to this method, occurrence of a new fracture due to striking the substrate can be prevented, and a collision sound produced at the time of striking can be reduced.

In addition, for the elastic member, a member with a Shore hardness of approximately 40~60 is preferably used. This is because extracting a characteristic sound tends to become difficult with a higher or lower hardness.

In addition, it is preferable to support a center part of the substrate and provide vibration for a peripheral part of the substrate. In addition, the substrate is preferably supported by use of a vacuum suction pad. Furthermore, it is preferable to use one vacuum suction pad whose size has an area of approximately 5~10% of the wafer size. As the material of the suction pad, a synthetic rubber base whose Shore is approximately 40~60 is preferable. The substrate is preferably supported at one position. This is because outputting a characteristic sound at the time of striking becomes difficult if the substrate is held at a plurality of positions.

Next, description will be given of the step (2), namely, a step of determining a power spectrum by capturing the produced sound and carrying out an acoustic analysis for the captured sound.

The produced sound can be captured by use of, for example, an element for converting a sound wave to an electrical signal such as a microphone. In addition, a microphone having flat frequency characteristics at 20 Hz~20 KHz is preferably used.

As the acoustic analysis, an FFT analysis, an octave analysis, etc., are included. "Determining a power spectrum" means determining, by carrying out a Fourier transformation for a captured sound, a power spectrum of the sound. The power spectrum indicates spectral intensities of each sample frequency band.

Next, description will be given of the step (3), namely, a step of judging whether or not a substrate crack exists based on a spectral intensity of a predetermined frequency region.

The substrate crack means a crazing, fissure, or chipping formed inside or on the surface of a substrate, etc. The predetermined frequency region means a frequency region where a difference is produced in the spectral intensities depending on the presence and absence of a substrate crack. Accordingly, by previously defining this frequency region by an experiment, etc., and estimating a spectral intensity of the frequency region, whether or not a substrate crack exists is judged.

The inventor has discovered that the spectral intensity increases at a high-frequency region of 7 KHz or more. Thereby, it becomes possible to judge whether or not a substrate crack exists based on the spectral intensity of the high-frequency region of 7 KHz or more.

In addition, it is preferable to judge whether or not a substrate crack exists based on a spectral intensity of an audible frequency region of 10 KHz or more and 20 KHz or less. If the spectral intensity of this region is used, a commercially available reasonably priced microphone can be used, whereby the apparatus cost can be reduced.

A substrate crack inspecting method according to a second embodiment of the present invention comprises the steps of (1) providing vibration for a plurality of positions on a substrate in order, and each time vibration is provided, determining a power spectrum by capturing a sound produced by the vibration and carrying out an acoustic analysis for the captured sound, (2) statistically analyzing spectral intensities of a predetermined frequency region for a plurality of obtained power spectrums, and judging whether or not a substrate crack exists based on the result of analysis.

First, description will be given of the step (1), namely, the step of providing vibration for a plurality of positions on a substrate in order, and each time vibration is provided, determining a power spectrum by capturing a sound produced by the vibration and carrying out an acoustic analysis for the captured sound.

In the second embodiment, vibration is provided for a plurality of positions on a substrate, and a power spectrum is determined each time the vibration is provided. Thereby, power spectrums for the respective positions of the substrate are obtained.

If vibration is provided for only one position, a substrate crack cannot sometimes be detected depending on the relationship between the position of the crack and position where vibration is provided, however, by providing vibration for a plurality of positions, a substrate crack can be detected with accuracy irrespective of the relationship between the position of the crack and positions where vibration is provided.

In addition, since each power spectrum reflects the position and size of a substrate crack, by analyzing a plurality of power spectrums, information concerning the position and size of a substrate crack can be obtained with a higher accuracy, and this can be used for specifying the origin of a substrate crack.

Figure 1:
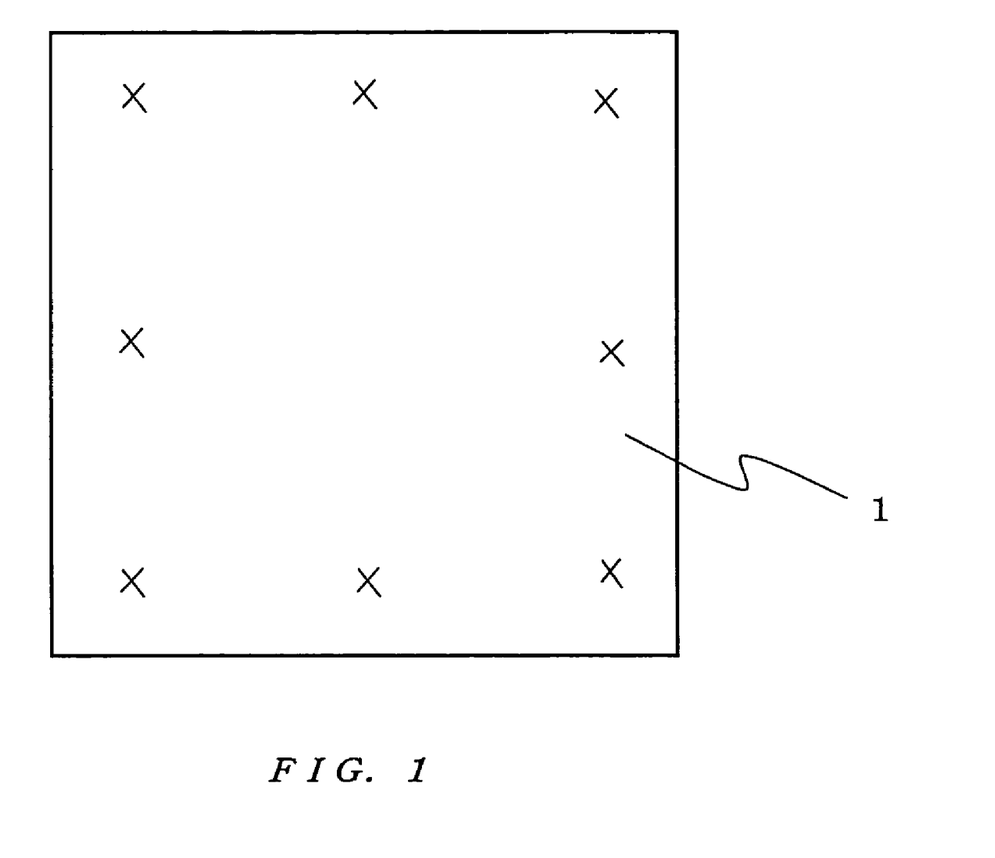
FIG. 1 is a plan view showing an example of striking points on the substrate according to the present invention.

It is preferable that the positions where vibration is provided are uniformly arranged in the periphery of the substrate. In addition, at this time, a center part of the substrate is preferably supported, preferably, by use of a vacuum suction pad. Concretely, for example, as shown by x marks in FIG. 1, vibration can be provided for four corner points and four points of side center portions of a substrate 1.

Next, description will be given of the step (2), namely, the step of statistically analyzing spectral intensities of a predetermined frequency region for a plurality of obtained power spectrums and judging whether or not a substrate crack exists based on the result of analysis.

The statistical analysis means, for example, counting, out of a plurality of power spectrums, power spectrum(s) whose spectral intensity is a predetermined threshold value or more and judging whether or not a substrate crack exists based on the result.

Concretely, for example, power spectrums are determined for eight points of the substrate, and if a spectral intensity of a predetermined frequency region is a threshold value or more even at one point thereof, it can be judged that a substrate crack exists, and in addition, in consideration of a detection error, etc., owing to various factors, for example, if a spectral intensity of a predetermined frequency region is a threshold value or more at four points or more, it can be judged that a substrate crack exists. Moreover, by comparing spectral intensities of a predetermined frequency region of respective power spectrums with each other and comprehensively judging the result thereof, whether or not a substrate crack exists may be judged. In any case, by carrying out a statistical analysis for a plurality of power spectrums, whether or not a substrate crack exists can be judged more accurately than in a case where one power spectrum is used.

In regard to the second embodiment, other matters are common to those of the first embodiment, and the description of the first embodiment applies thereto.

In view of another aspect, the present invention provides a solar battery module manufacturing method comprising the steps of (1) inspecting a plurality of solar battery cells by the substrate crack inspecting method as described above, selecting solar battery cells without substrate cracks, and (2) electrically connecting the plurality of selected solar battery cells for modularization.

As the solar battery cells, solar battery cells formed by use of elemental semiconductors of polycrystalline, monocrystalline silicon, etc., and compound semiconductors of GaAs, etc., are included.

"Electrically connecting" means connecting a plurality of solar battery cells mutually, for example, in series by use of a conductive member such as an interconnector. In addition, mutually connecting a plurality of solar battery cells directly without using a conductive member is also included.

"Modularization" means electrically connecting a plurality of solar battery cells to form arrayed cells, and furthermore, laminating tempered glass, a sealing resin, arrayed cells, a sealing resin, and a back film in this order, carrying out sealing processing after connecting the adjacent arrayed cells and attaching power drawout terminal lines, and attaching a terminal box to the power drawout terminal lines and attaching a frame are also included.

By not charging solar battery cells with substrate cracks by carrying out, for a plurality of solar battery cells, an inspection by the substrate crack inspecting method, a cell fracture in the modularization steps can be prevented beforehand, whereby productivity can be improved.

In view of another aspect, the present invention provides a substrate crack inspection apparatus comprising: an openable/closable hollow airtight container; an airtight container opening/closing portion for opening/closing the hollow airtight container; a substrate supporting portion for supporting a substrate provided in the airtight container; a striking portion for striking the substrate provided and supported in the airtight container; a sound collecting portion for collecting a striking vibration sound of the substrate provided in the airtight container; and an acoustic analysis portion for carrying out an acoustic analysis of the striking vibration sound collected by the sound collecting portion and judging whether or not a substrate crack exists based on an obtained power spectrum.

In the substrate crack inspection apparatus of the present invention, since the substrate is struck in the airtight container and its striking vibration sound is collected, without being affected by a noise outside the container, an accurate inspection is possible.

The openable/closable hollow airtight container is composed of, for example, two containers separable into a top and bottom, and this can be opened and closed by being separated by an airtight container opening/closing portion. In addition, the hollow airtight container can have, in its one airtight container, opening/closing means such as doors or shutters at one or a plurality of positions. In this case, a substrate carried in through an opening/closing position may be carried out through the identical opening/closing position or may be carried out through another opening/closing position.

The airtight container can be formed of a commercially available appropriate sound insulating material such as glass wool. In addition, it is preferable to apply, to the part divided for opening/closing, a measure to prevent a noise intrusion by means of a sealing material such as sound insulating synthetic rubber.

For the airtight container opening/closing portion, an opening/closing mechanism powered by a hydraulic cylinder or an electric motor can be used.

For the substrate supporting portion, a vacuum suction member, for example, a vacuum suction pad is preferably used. This is because an excessive shock by the striking portion can be absorbed and thereby fracture of the substrate as a result of a stress concentration upon the supporting portion can be prevented. For easily receiving the substrate from a carrying portion, which will be described later, the vacuum suction pad is preferably installed inside the airtight container, via a cylinder or the like to shift the vacuum suction pad up and down.

The striking portion is attached inside the airtight container and strikes the substrate by using a driving force by a motor or a hydraulic cylinder or a spring elastic force. The striking portion is preferably formed of a synthetic rubber whose Shore is approximately 40~60.

A plurality of striking portions may be provided to strike a plurality of positions of the substrate, and moreover, a means for rotating the substrate and/or a means for horizontally shifting the substrate is provided so as to strike a plurality of positions of the substrate by rotating the substrate, horizontally shifting the substrate, and/or a combination thereof.

For the sound collecting portion, an element for converting a sound wave to an electrical signal can be used, and for example, a microphone can be used. For the microphone, a microphone having flat frequency characteristics at 20 Hz~20 KHz is preferably used.

As the acoustic analysis portion, an element having a program for carrying out, by use of a microcomputer, a Fourier transformation of a striking vibration sound and judging whether or not a substrate crack exists based on the obtained power spectrum can be used.

In addition, a carrying portion for carrying in and out a substrate to be inspected with respect to the airtight container, a substrate housing portion for housing a carried-out substrate, and a control portion for controlling the carrying portion based on the judgment result of the acoustic analysis portion to sort the substrates depending on whether or not a substrate crack exists and make the substrate housing portion house the same may further be provided.

As the carrying portion, a carrying portion by a belt conveyer method, a walking beam method, a pickup method, etc., can be used. In the pickup method, it is preferable that a vacuum suction pad is provided at a front end portion of a movable arm so as to support the substrate. In addition, the vacuum suction pad is, for easily picking up the substrate, preferably attached to the movable arm via a cylinder or the like to shift the vacuum suction pad up and down.

The substrate housing portion may be a container to house substrates or may be a stand on which substrates are placed. The substrate housing portion is preferably sectioned into a plurality of sections to sort substrates into the respective sections according to whether or not a substrate crack exists.

According to the substrate crack inspection apparatus of the present invention, inspected substrates are sorted out according to whether or not a substrate crack exists and are housed in the substrate housing portion. According to this apparatus configuration, cells with cracks are sent to a re-inspection or elimination step, and only cells without cracks can be supplied to the solar battery module manufacturing steps.

EXAMPLE 1

A substrate crack inspecting method according to Example 1 of the present invention will be described by use of FIGS. 2(a) and (b).

As an inspection target, a solar battery cell 11 whose size is a 126 mm-square and whose thickness is approximately 200μ~300μ is used (hereinafter, referred to as a "substrate".) The substrate 11 is, at near the center thereof, suctioned and held by a φ30~40 mm-round silicon vacuum suction pad 13.

With regard to the striking apparatus, it is desirable to produce only a collision sound against a wafer at the moment of striking, and using such a mechanism is necessary. The striking hammer is sent down until it collides against the wafer surface and the produced sound is collected.

Figure 2:
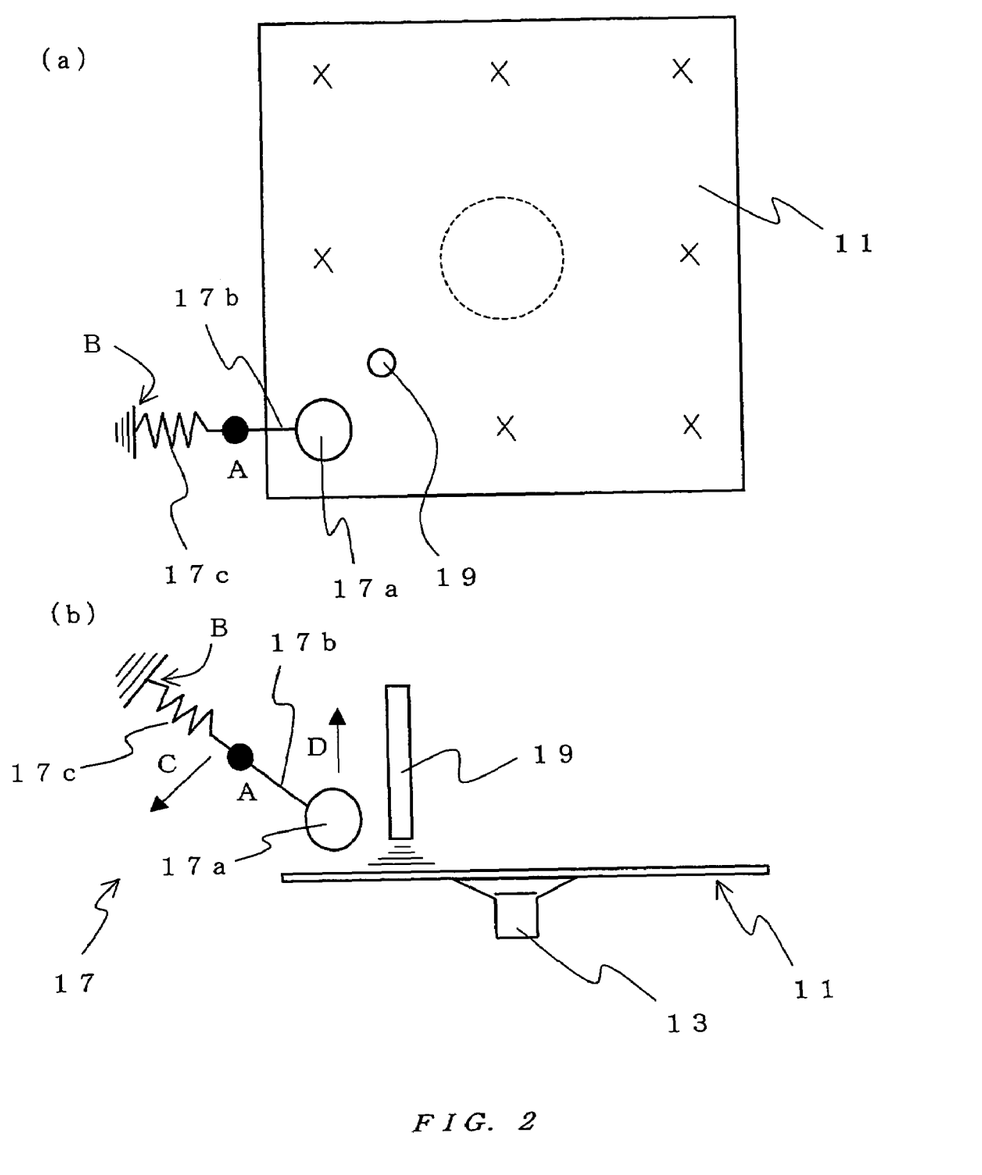
FIG. 2 is a plan view and a side view showing an outline of the method according to Example 1 of the present invention.

In Example 1, striking is realized by use of a mechanism as shown in FIG. 2(b). A substrate striking portion 17a is connected to a striking hammer supporting bar 17b. The striking hammer supporting bar 17b is supported by a striking hammer supporting shaft A and a spring 17c. In addition, since the spring 17c is held by a fixing end B, the substrate striking portion 17 is linearly held. In the condition supported by a spring force, by operating a spring-side part of the striking hammer supporting bar 17b in the direction of arrow C by means of a cam mechanism (unillustrated), the striking hammer supporting bar 17b is rotated around the striking hammer supporting shaft A and the substrate striking portion 17a is shifted in the direction of arrow D. Thereafter, when the cam mechanism releases the striking hammer supporting bar 17b, as a result of a restoring force of the spring 17c, the substrate striking portion 17a receives a force in the wafer direction and strikes the wafer 11. The substrate striking portion 17a then carries out an oscillating movement with attenuation. A collision sound is produced at this time.

By use of this mechanism, whether or not a crack exists is judged by the following procedures. First, a vibration is provided for the substrate 11 by striking, from the side opposite the surface suctioned by the vacuum suction pad 13, the substrate 11 at a strength for which a static load onto the substrate 11 becomes approximately 80 g. A lump of synthetic rubber whose Shore is approximately 40~60 and which has a nearly spherical curved surface shape is attached to the substrate striking portion 17a.

A sound produced by striking is captured by use of a microphone 19 having flat frequency characteristics at 20 Hz~20 KHz. An octave analysis is carried out for the captured sound to determine a power spectrum.

Herein, as shown by x marks in FIG. 2(a), a total of eight striking points of four corner points and four points of side center portions of the substrate are struck, and for each striking point, an octave analysis is carried out to determine a power spectrum.

Figure 3:
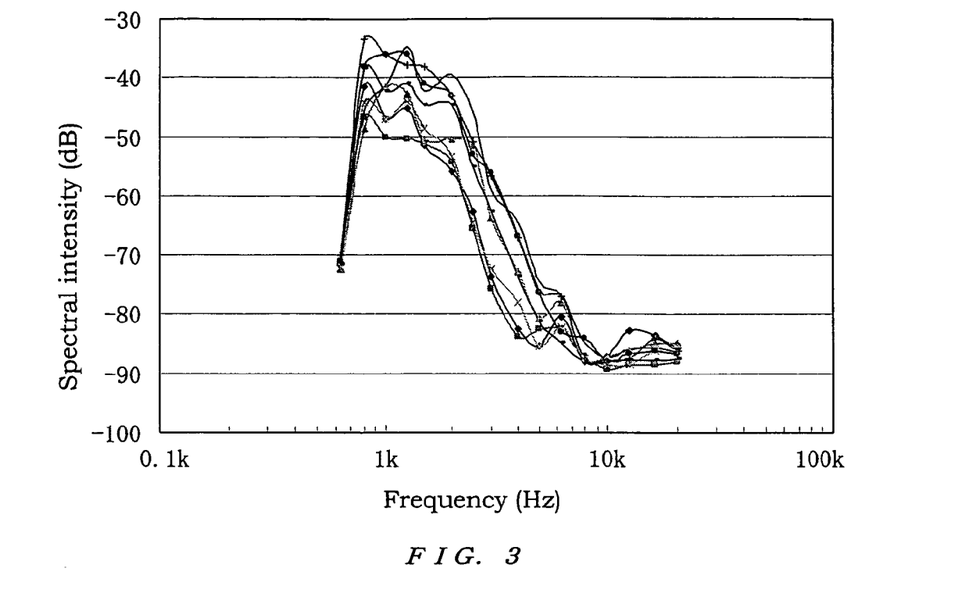
FIG. 3 shows power spectrums of a substrate without a substrate crack according to the present invention.
Figure 4:
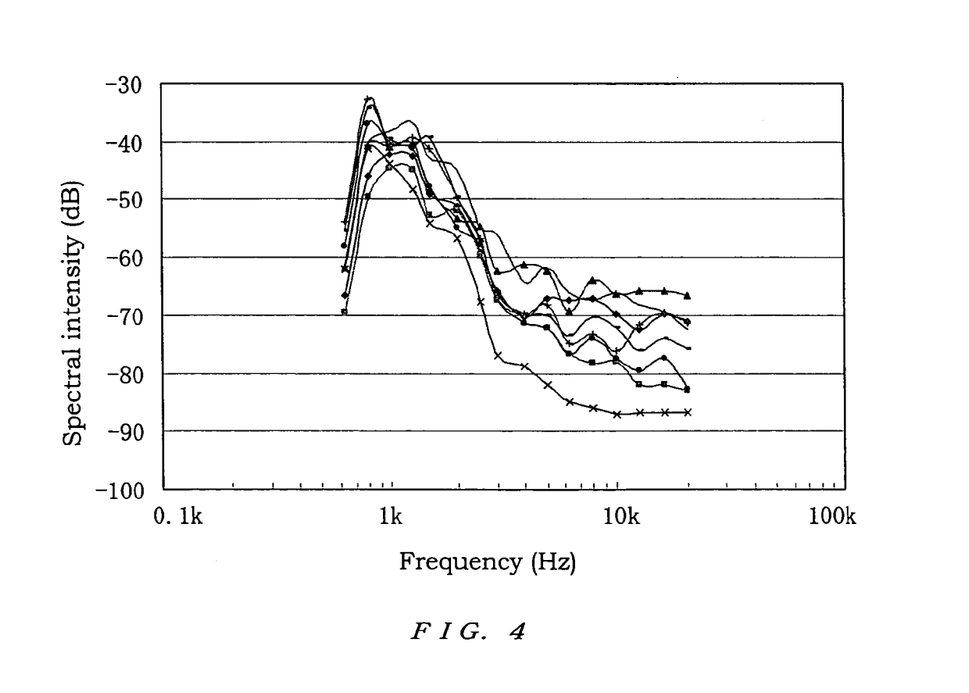
FIG. 4 shows power spectrums of a substrate with a substrate crack according to the present invention.

Results of octave analyses by the method as described above are shown in FIGS. 3 and 4. FIG. 3 shows power spectrums of a substrate without a substrate crack (normal substrate), and FIG. 4 shows power spectrums of a substrate with a substrate crack (abnormal substrate). In both drawings, eight power spectrums respectively obtained from eight striking points are shown.

In the region with a frequency of 8 kHz or more, spectral intensities of all power spectrums shown in FIG. 3 are stable in a range of −80~−90 dB, whereas spectral intensities of the power spectrums shown in FIG. 4 are varied with −60~−90 dB.

Whether or not a substrate crack exists is judged based on the difference. For judgment, respective threshold values at 8 kHz, 10 kHz, 12.5 kHz, 16 kHz, and 20 kHz after an octave analysis are set to, for example, −75 dB, −75 dB, −80 dB, −80 dB, and −85 dB. Although no striking point exceeding its threshold value exists in the normal substrate, there are seven striking points exceeding their threshold values in the abnormal substrate. By adding the number of striking points exceeding the threshold values to the screening criteria, a wider range of judgment can be provided for a subtle judgment.

As can be understood from FIG. 4, depending on the striking position, a striking point where, at 8 kHz, 10 kHz, 12.5 kHz, 16 kHz, and 20 kHz, spectral intensities all result in −80 dB or less exits, and there is a possibility that the substrate is judged to be a normal substrate despite an abnormal substrate. Accordingly, it is understood that the judging accuracy is improved by striking a plurality of points.

EXAMPLE 2

Figure 5:
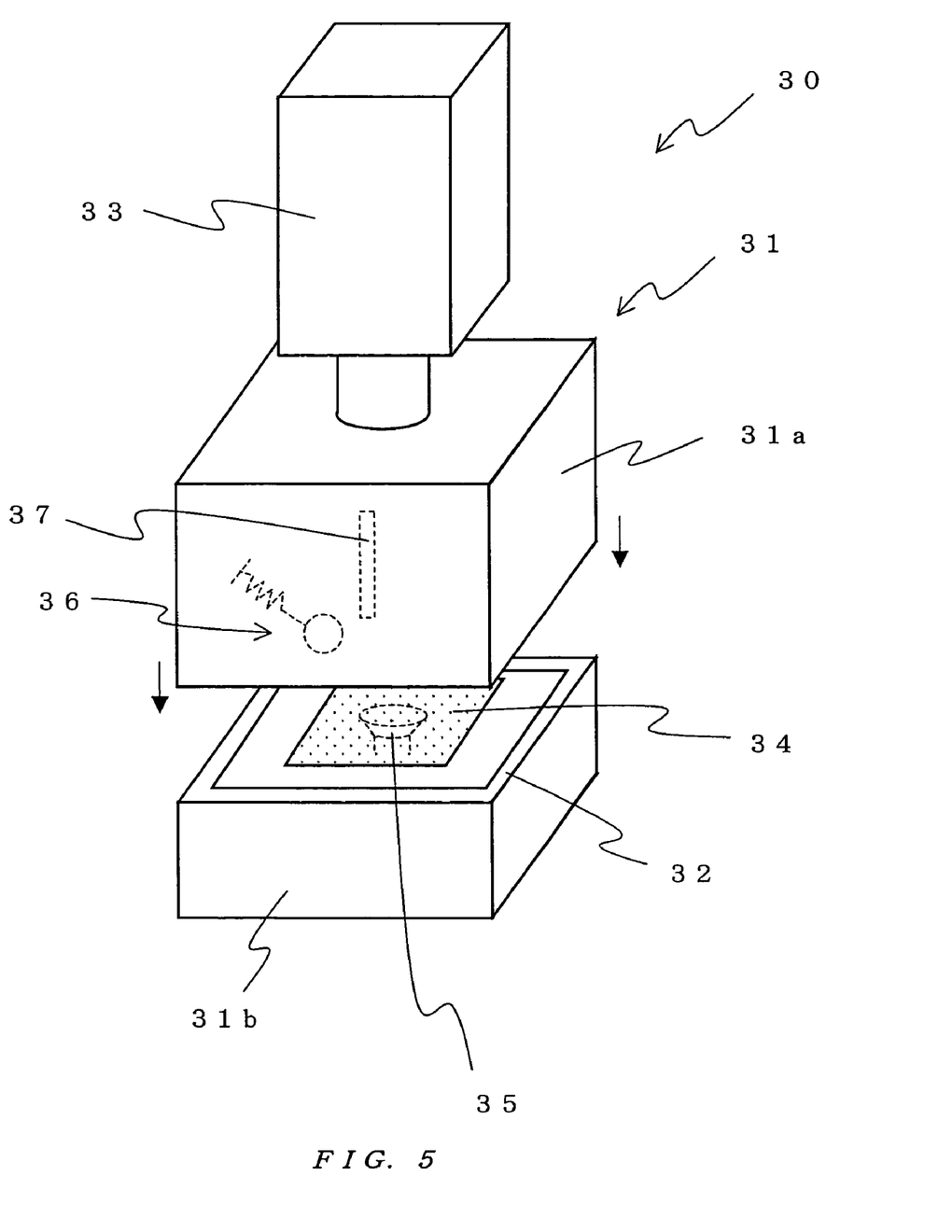
FIG. 5 is a perspective view showing an outline of the substrate crack inspection apparatus according to Example 2 of the present invention.
Figure 6:
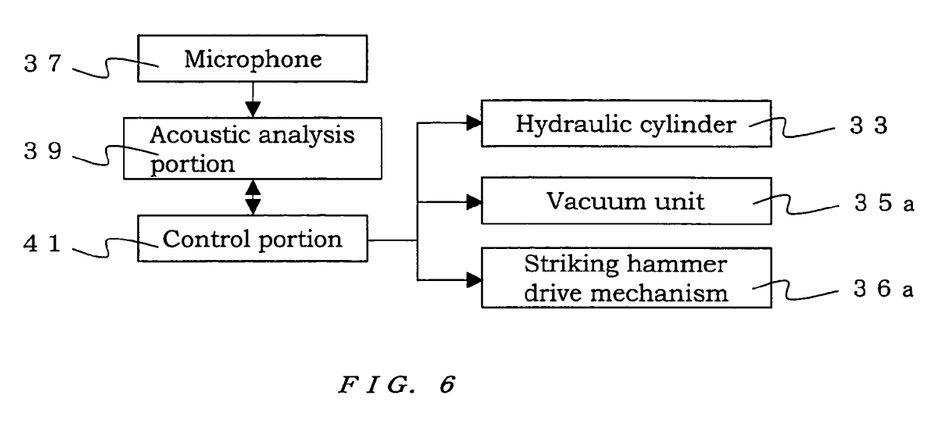
FIG. 6 is a block diagram of a controller of the substrate crack inspection apparatus according to Example 2 of the present invention.

FIG. 5 shows a substrate crack inspection apparatus according to Example 2. FIG. 6 shows a block diagram of its controller. As shown in FIG. 5, a substrate crack inspection apparatus 30 is provided with an openable/closable hollow airtight container 31 composed of an upper container 31a and a lower container 31b and a hydraulic cylinder for opening/closing the upper container 31a. Inside the airtight container 31, a vacuum suction pad 35 for supporting a substrate 34 provided in the airtight container 31, a striking hammer 36 for striking the substrate 34 provided and supported in the airtight container 31, and a microphone 37 for collecting a striking vibration sound of the substrate 34 are provided.

As shown in FIG. 6, the controller is provided with an acoustic analysis portion 39 which carries out an acoustic analysis for a striking vibration sound collected by the microphone 37 and judges whether or nor a substrate crack exists based on an obtained power spectrum, a hydraulic cylinder 33, a vacuum unit 35a for actuating the vacuum suction pad 35, a striking hammer drive mechanism 36a for driving the striking hammer, and a control portion 41, and the control portion 41 controls the acoustic analysis portion 39, hydraulic cylinder 33, vacuum unit 35a, and striking hammer drive mechanism 36a.

Here, the airtight container 31 is formed of glass wool, which is a sound insulating material. The acoustic analysis portion 39 and control portion 41 are integrally formed by use of a microcomputer. For the vacuum unit 35a, a commercially available vacuum pump is used. In addition, by providing a synthetic rubber packing 32 for the part divided into the upper container 30a and lower container 30b, a measure against noise intrusion from the outside is taken. For the striking hammer drive mechanism 36a, a mechanism the same as that described by use of FIG. 2 in Example 1 is used.

By use of this apparatus, an inspection was carried out for the effect of the airtight container 31. The results are shown in FIG. 7 and FIG. 8.

Figure 7:
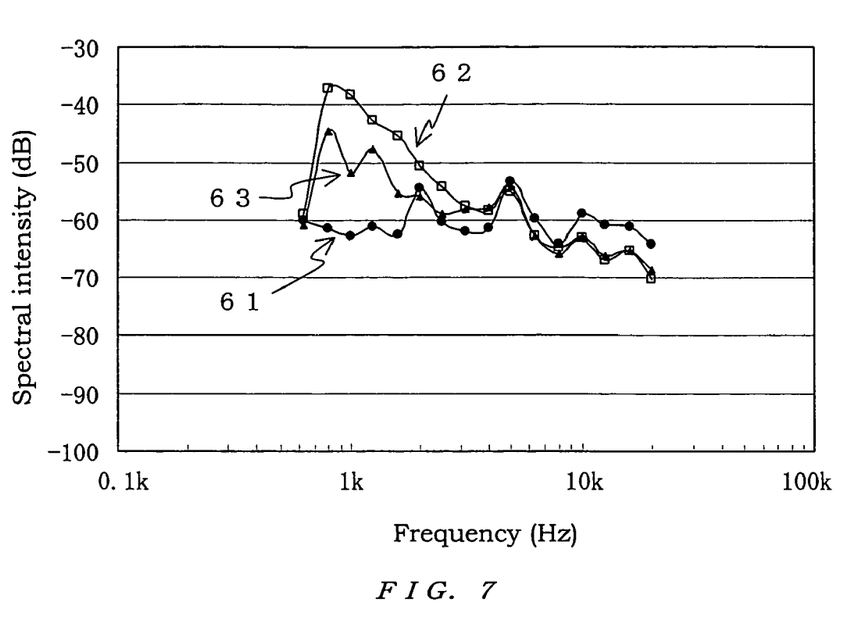
FIG. 7 shows power spectrums measured with the airtight container opened according to the present invention.

FIG. 7 shows a result of an inspection carried out in terms of whether or not a substrate crack existed in a condition where the airtight container 31 was opened. Curve 61 is an example of an on-site sound in a manufacturing line, which is approximately −60 dB at each frequency band. As a matter of course, an unexpected sound may be produced, and a great difference often exists depending on the place. Curve 62 is an example of a condition where a normal wafer was struck in the manufacturing line and curve 63 is an example of a condition where an abnormal wafer was struck in the manufacturing line, wherein a sound pressure difference is small at 8K~20 KHz. Namely, a distinction between the normality and abnormality tends to be difficult. Furthermore, since there are influences of an unexpected sound and depending on the place, distinction is difficult.

Figure 8:
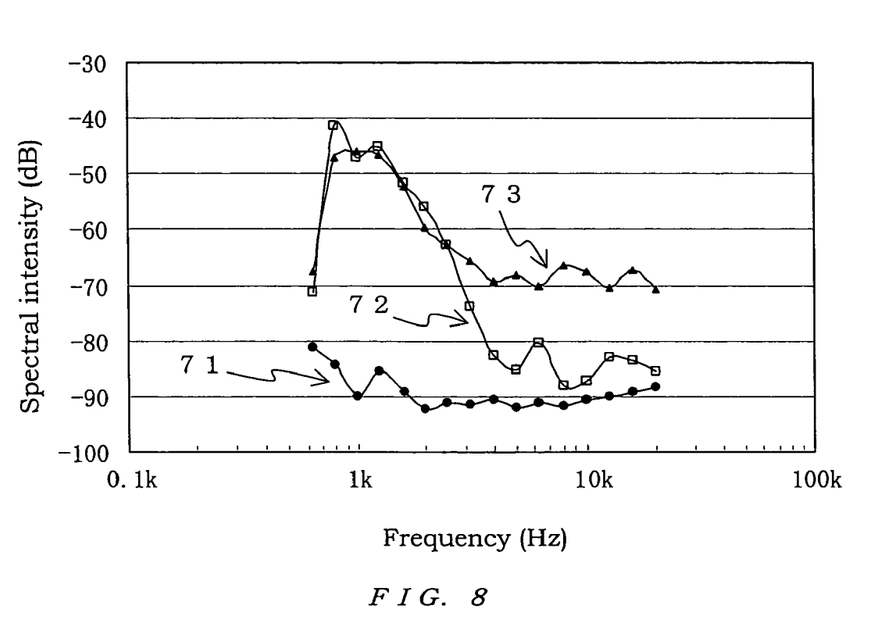
FIG. 8 shows power spectrums measured with the airtight container closed according to the present invention.

FIG. 8 shows a result of an inspection carried out in terms of whether or not a substrate crack existed in a condition where the airtight container was closed. Curve 71 is an example of environmental sound data at the inside surrounded by a sound insulating material, curve 72 is an example of a condition where a normal wafer was struck at the inside surrounded by a sound insulating material, and curve 73 is an example of a condition where an abnormal wafer was struck at the inside surrounded by a sound insulating material, wherein compared to the case where striking was carried out in the manufacturing line environment, the sound pressure difference is great at around 8K~20 KHz. Based on these results, the present invention can provide an apparatus which is not affected by such an environmental noise.

EXAMPLE 3

Figure 9:
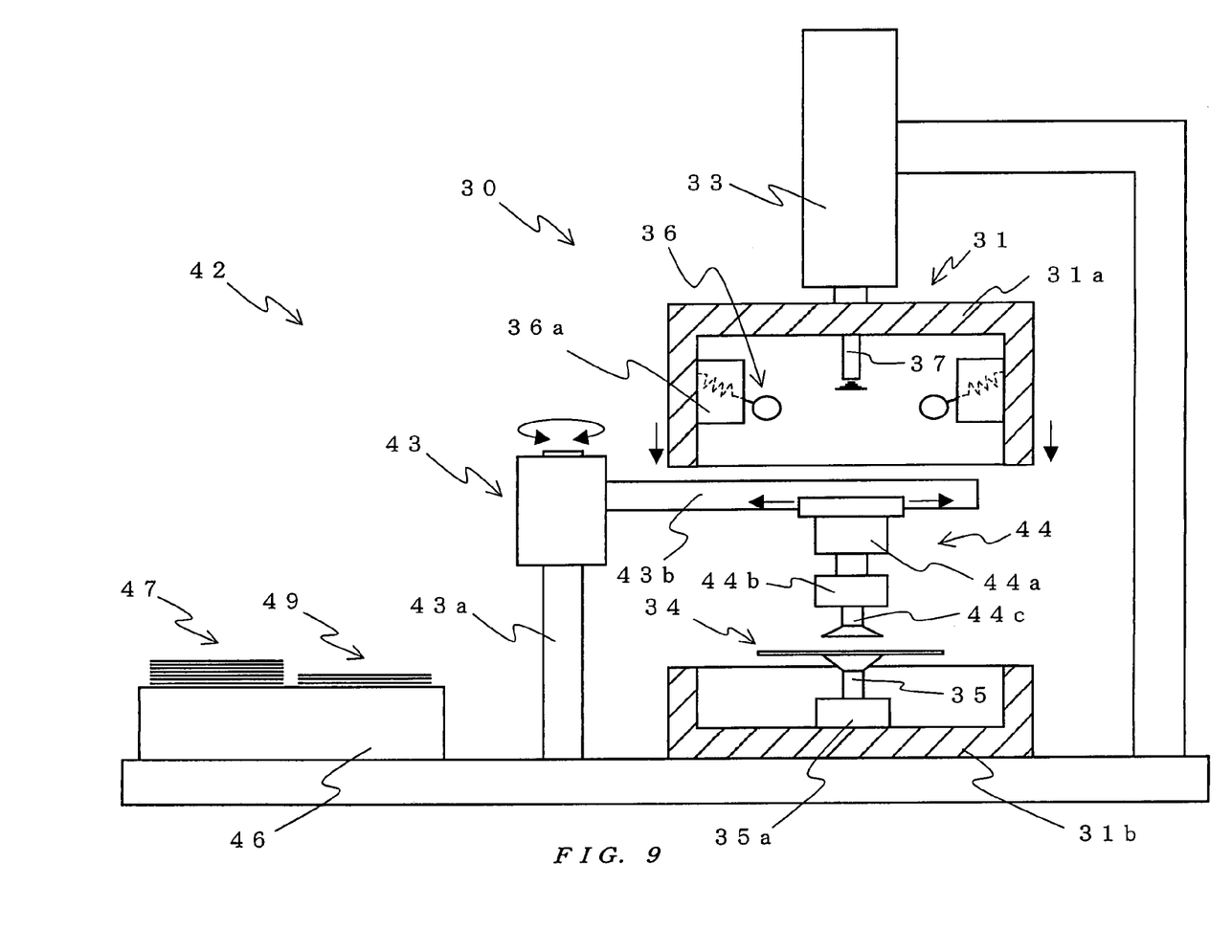
FIG. 9 is a side view showing an outline of the substrate crack inspection apparatus according to Example 3 of the present invention.
Figure 10:
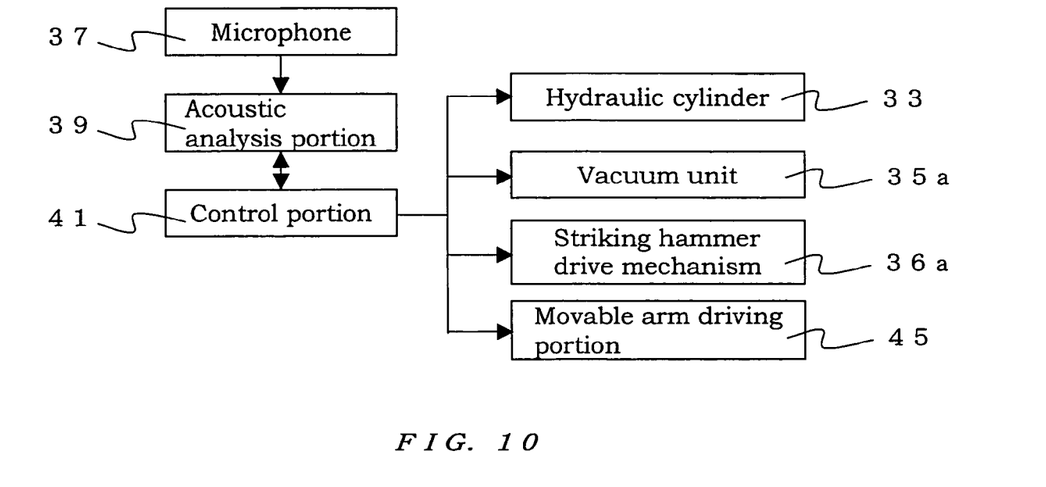
FIG. 10 is a block diagram of a controller of the substrate crack inspection apparatus according to Example 3 of the present invention.

FIG. 9 shows a substrate crack inspection apparatus 42 according to Example 3 of the present invention. FIG. 10 shows a block diagram of its controller. The substrate crack inspection apparatus 42 according to Example 3 is, in addition to the substrate crack inspection apparatus 30 according to Example 2 of the present invention, further provided with a movable arm unit 43 for carrying in and out a substrate 34 to be inspected with respect to the airtight container 31 and a substrate housing base 46 for housing a carried-out substrate 34. In the controller shown in FIG. 10, the control portion 41 further controls a movable arm driving portion 45 to, as will be described later, sort inspected substrates 34 into normal substrates 47 and abnormal substrates 49 depending on whether a substrate crack exists and house the same in the substrate housing portion 46. Other aspects of the configuration are the same as those of FIG. 2.

As shown in FIG. 9, the movable arm unit 43 is provided with a shaft 43a, a movable arm 43b attached to the shaft 43a so as to be rotatable in the horizontal direction, and a movable arm head 44 attached to the movable arm 43b so as to be shiftable in the horizontal direction. The movable arm 43b rotates around the shaft 43a and shifts to the inside and outside of the airtight container 31. The movable arm head 44 can freely shift along the longitudinal direction of the movable arm 43b. In addition, the movable arm head 44 is provided with a hydraulic cylinder 44a, a vacuum unit 44b, and a vacuum suction pad 44c, which are attached in order from the movable arm 43b. The movable arm 43b and movable arm head 44 are driven by the movable arm driving portion 45.

By combining the rotation of the movable arm 43b and horizontal shift of the movable arm head 44, the movable arm unit 43 carries a not-yet-inspected substrate placed outside the airtight container 31 into the airtight container 31, sorts out inspected substrates 32 into normal substrates 47 and abnormal substrates 49 depending on whether a substrate crack exists, and houses the same in the substrate housing portion 46.

According to this apparatus configuration, cells with cracks are sent to a re-inspection or elimination step, and only cells without cracks can be supplied to the solar battery module manufacturing steps.

Figure 11:
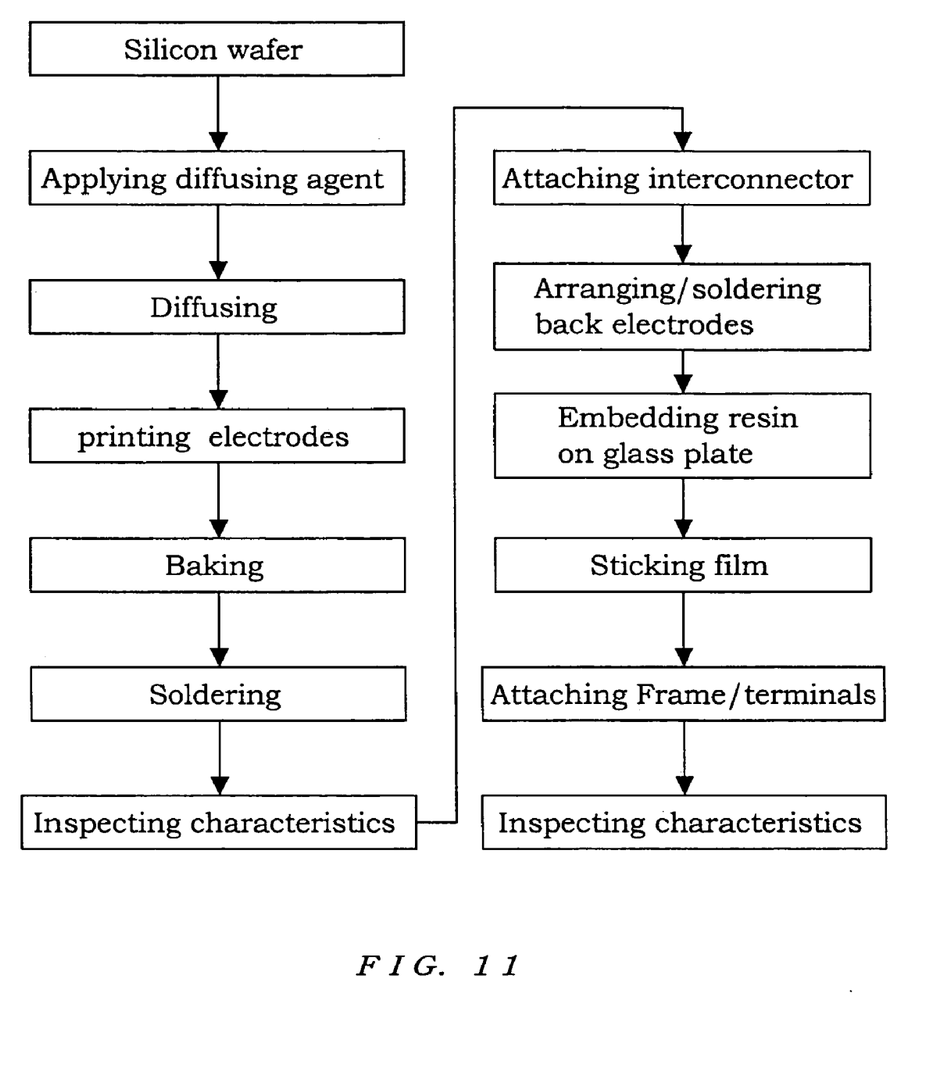
FIG. 11 shows an example of solar battery manufacturing steps to which the present invention is applied.

Next, description will be given of solar battery module manufacturing steps to which the substrate crack inspection apparatus is applied. In the general manufacturing steps shown in the flowchart of FIG. 11, solar battery cells (wafers) are completed at the point in time where the soldering step is finished, and then the wafers shift to a module assembling step. In this case, since damage and microcrack progression, etc., can occur depending on the packing and transferring methods, an acceptance inspection is carried out before the module manufacturing steps. The method and apparatus according to the present invention can be used, after the completion of cells and after sorting according to electrical characteristics by a characteristics inspection step, in the acceptance inspection and any subsequent steps.

What is claimed is:

1. A substrate crack inspecting method comprising the steps of (1) producing a sound by providing vibration for a peripheral part of a substrate, with the substrate being supported at only one position at a center portion of the substrate, (2) determining a power spectrum by capturing the produced sound and carrying out an acoustic analysis for the captured sound, and (3) judging whether or not a substrate crack exists based on a spectral intensity of a predetermined frequency region.

2. The substrate crack inspecting method as set forth in claim 1, further comprising supporting a center part of the substrate by use of a vacuum suction pad.

3. The substrate crack inspecting method as set forth in claim 1, wherein the predetermined frequency region is a high-frequency region of 7 KHz or more.

4. The substrate crack inspecting method as set forth in claim 1, wherein the predetermined frequency region is an audible frequency region of 10 KHz or more and 20 KHz or less.

5. A solar battery module manufacturing method comprising the steps of (1) inspecting a plurality of solar battery cells by the substrate crack inspecting method as set forth in claim 1, selecting solar battery cells without substrate cracks, and (2) electrically connecting the plurality of selected solar battery cells for modularization.

6. A substrate crack inspecting method comprising the steps of (1) providing vibration for a plurality of positions on a peripheral part of a substrate in order, with the substrate being supported at only one position at a center portion of the substrate, and each time vibration is provided determining a power spectrum by capturing a sound produced by the vibration and carrying out an acoustic analysis for the captured sound, (2) statistically analyzing spectral intensities of a predetermined frequency region for a plurality of obtained power spectrums, and judging whether or not a substrate crack exists based on the result of analysis.

7. The substrate crack inspecting method as set forth in claim 6, wherein the step of providing vibration for a substrate is a step of providing vibration for a substrate by striking the substrate by an elastic member while supporting a predefined part of the substrate.

8. The substrate crack inspecting method as set forth in claim 6, wherein the acoustic analysis is an octave analysis.

9. A substrate crack inspection apparatus comprising:
an openable/closable hollow airtight container;
an airtight container opening/closing portion for opening/closing the hollow airtight container;
a substrate supporting portion for supporting a substrate at only one position at a center portion of the substrate, the substrate supporting portion being provided in the airtight container;
a striking portion for striking a peripheral part of the substrate provided and supported in the airtight container;
a sound collecting portion for collecting a striking vibration sound of the substrate provided in the airtight container; and
an acoustic analysis portion for carrying out an acoustic analysis of the striking vibration sound collected by the sound collecting portion and judging whether or not a substrate crack exists based on an obtained power spectrum.

10. The substrate crack inspection apparatus as set forth in claim 9, further comprising: a carrying portion for carrying in and out a substrate to be inspected with respect to the airtight container; a substrate housing portion for housing a carried-out substrate; and a control portion for controlling the carrying portion based on the judgment result of the acoustic analysis portion to sort the substrates depending on whether or not a substrate crack exists and make the substrate housing portion house the same.

* * * * *